United States Patent [19]

Paulus et al.

[11] Patent Number: 5,429,583
[45] Date of Patent: Jul. 4, 1995

[54] COBALT PALLADIUM SEEDS FOR THERMAL TREATMENT OF TUMORS

[75] Inventors: Joseph A. Paulus, Iowa City; Robert D. Tucker, North Liberty, both of Iowa

[73] Assignee: Pegasus Medical Technologies, Inc., Minneapolis, Minn.

[21] Appl. No.: 164,468

[22] Filed: Dec. 9, 1993

[51] Int. Cl.⁶ .............................................. A61N 5/00
[52] U.S. Cl. ..................................... 600/2; 600/8
[58] Field of Search ........................................ 600/1–7

[56] References Cited

U.S. PATENT DOCUMENTS

| | | |
|---|---|---|
| 3,653,385 | 4/1972 | Burton . |
| 4,106,488 | 8/1978 | Gordon . |
| 4,323,056 | 4/1982 | Borrelli et al. . |
| 4,610,241 | 9/1986 | Gordon . |
| 4,735,772 | 4/1988 | van der Zel . |
| 4,735,796 | 4/1988 | Gordon . |
| 4,763,671 | 8/1988 | Goffinet ........................... 600/7 |
| 4,813,399 | 3/1989 | Gordon . |
| 4,889,120 | 12/1989 | Gordon . |
| 4,923,437 | 5/1990 | Gordon . |
| 4,950,221 | 8/1990 | Gordon . |
| 4,996,991 | 3/1991 | Gordon . |
| 5,087,438 | 2/1992 | Gordon . |
| 5,133,710 | 7/1992 | Carter, Jr. et al. . |

FOREIGN PATENT DOCUMENTS

| | | | |
|---|---|---|---|
| 5049704 | 3/1993 | Japan ..................................... | 600/2 |

OTHER PUBLICATIONS

"Pd–Co Dental Casting Ferromagnetic Alloys" by Kinouchi et al, J. Dent Res. Jan. 1981, pp. 50–58.

"The Magnetic Properties of Certain Pt–Co and Pd–Co Alloys" by F. Woodbridge Constant, Dec. 1, 1980 Physical Review, vol. 36, pp. 1654–1660.

"Practical Aspects of Ferromagnetic Thermoseed Hyperthermia" by Ivan Brezovich et al, pp. 589–602.

"Cytotoxicity of Pd–Co Dental Casting Ferromagnetic Alloys" by A. Kawata, et al., J. Dent Res, Aug. 1991, vol. 60, No. 8, pp. 1403–1409.

"Local Hypothermia with Interstitial Techniques" by Ivan Brezovich et al, Cancer Research (Suppl.) vol. 44, Oct. 1984, pp. 4752s–4756s.

"Ferromagnetic Alloys with Curie Temperatures Near 50° C. for Use in Hyperthermic Therapy" Hyperthermic Oncology, by R. Deshmukh, et al, pp. 571–574 vol. 1.

Thesis entitled "Charaterization of Nickel–Cooper Alloy Interstitial Thermoseeds for Induction Hyperthermia of the Prostate" by Scott Dale Ferguson, dated Dec. 1991.

Magnetic Properties of Alloys of Cobalt and Nickel with Palladium and Plantinum by E. P. Wohlfarth, Correspondence Ser. 7, vol. 45, No. 365, Jun. 1954, pp. 647–649.

"Effect of Thermal Treatment on Heating Charactistics of Ni–Cu Alloy for Hyperthermia: Preliminary Studies" by S. D. Ferguson et al, Jun. 1992.

"Power Adsorption in Ferromagnetic Implants from Radio Frequency Magnetic Fields and the Problem of Optimization" by Shah A. Haider et al, IEEE, vol. 39, No. 11, Nov. 1991, pp. 1817–1827.

*Primary Examiner*—William E. Kamm
*Assistant Examiner*—J. P. Lacyk
*Attorney, Agent, or Firm*—Haugen and Nikolai

[57] ABSTRACT

A COPd thermoseed for treating cancerous tissue. The alloy constituents are chosen such that the Curie point temperature thereof falls into a therapeutic range. Because its magnetization vs. temperature characteristic exhibits an increasing slope up to the Curie transition, thermoseeds fabricated from the alloy can be optimized about the maximum in the M-T curve.

10 Claims, 5 Drawing Sheets

_Fig. 4_

_Fig. 5a_

— FERROMAGNETIC
--- PARAMAGNETIC

_Fig. 5b_

— FERROMAGNETIC
--- PARAMAGNETIC

*Fig. 6*

A ——— BESSEL
B —·—·— x<<1
C ————— x>>1

*Fig. 7*

B = 0.0010979 x atan (H/3785.44) + 1.38339 x 10⁻⁶ x H

Fig. 9
— LINEAR
--- NONLINEAR

Fig. 10
— LINEAR
--- NONLINEAR

COBALT PALLADIUM SEEDS FOR THERMAL TREATMENT OF TUMORS

BACKGROUND OF THE INVENTION

1. Field of the Invention: This invention relates generally to apparatus and method for treating cancerous tissue through hyperthermia thermotherapy, and more particularly to an improved thermoseed exhibiting a combination of properties, such that when subjected to an oscillating magnetic field of a predetermined frequency and field strength, produces controlled heating of the tissue into which such seeds are implanted.

2. Discussion of the Prior Art: In a journal article entitled "Practical Aspects of Ferromagnetic Thermoseed Hyperthermia", published in the Radiologic Clinics of North America, Vol. 27, No. 3, dated May 1989, Ivan A. Brezovich and Ruby F. Meredith, both then with the University of Alabama at Birmingham, presented a general treatise on a method of treating tumors by interstitially implanting small pieces of ferromagnetic alloy wire into the tissue and then exposing the subject to an externally applied oscillating magnetic field of a predetermined frequency and field strength so as to cause inductive heating of the thermoseeds within the body. This paper points out that by selecting a ferromagnetic material having a proper Curie point, such thermoseeds become self-regulating when the temperature of the seed approaches the Curie point at which the material becomes non-magnetic. The Brezovich et al. paper further points out that while ferromagnetic elements, such as iron, nickel and cobalt have Curie points far above the therapeutic range, the Curie point can be lowered by mixing a non-magnetic element into a ferromagnetic base metal. Nickel mixed with palladium, copper and silicon as well as iron mixed with platinum are suggested.

The Borrelli et al. patent 4,323,056, assigned to Corning Glass Works, and entitled "Radio Frequency Induced Hyperthermia for Tumor Therapy", describes a method in which magnetic field suscepting crystals of a certain size, composition, concentration, and magnetic properties are injected into the cancerous tissue and then the area involved is subjected to a high frequency magnetic field to effect hysteresis heating and resultant hyperthermia. In particular, the patent discloses the use of iron-containing crystals incorporated into certain organic plastics used as a matrix.

Our research is shown that while iron and nickel alloys have been widely studied and candidates for thermoseeds in cancer treatment, cobalt alloys have not received significant attention for a number of reasons. First, the Curie temperature of cobalt is 1130° C. compared to values of 358° C. and 770° C. for nickel and iron, respectively. This is believed to explain why so much attention has been devoted to the study of nickel binary alloys. According to metallurgical theory of magnetic alloys, nonmagnetic additions to ferromagnetic elements should lower the magnetization (magnetic permeability) of the material, as well as lowering the Curie temperature. Thus, alloys with low Curie points will have significantly poorer magnetic properties, corresponding to less heating power output below the Curie point for thermoseeds. Since nickel has the lowest initial Curie point, there will need to be lesser amounts of non-magnetic impurity need be added to bring the Curie temperature to the therapeutic range. Thus, following that logic, nickel alloys should retain their magnetic permeability better than iron or cobalt.

In addition to Curie point depression and magnetic permeability decline, non-magnetic additives to ferromagnetic elements tend to broaden the Curie transition from a few degrees C., to tens of degrees. A 1938 French scientist, Victor Marian, conducted numerous analyses of nickel alloys and found that many of the alloys had transitions of 50° C. to 100° C. when the ferromagnetic component was reduced to a few percent. This is believed to be the reason why, until now, other investigators have used nickel silicon alloy for their thermoseed experiments, as only 7% silicon reduces the Curie point of its alloy with nickel to 50° C. which is in the therapeutic range, while maintaining a fairly sharp Curie transition.

We have found that a cobalt palladium (CoPd) alloy does not match the standard pattern of binary magnetic alloys due to polarization of the palladium atoms. Even if as little as 5% Co is present, the magnetic transition of the alloy is still on the order of only 2° C.-3° C. and significant magnetization, and therefore heating power, is retained until the transition zone is reached. However, the magnetic permeability of the CoPd material is not as strong as for some of the other materials which have been the subject of investigation for use as thermoseeds.

Experiments that we have conducted, in which the magnetization of the CoPd alloy is plotted against temperature, reveals an interesting and rather unexpected result. Specifically, the permeability of this alloy is found to increase with heating in a range below the Curie point until the Curie transition is reached. As a result, implants fabricated from the alloy and the external field generator can be designed so that the seeds will radiate increasing amounts of power as they heat, until the Curie transition point is reached. By optimizing the implant about this local peak in the M vs. T curve, a highly efficient on-off switch can be constructed, with maximum power output within a few degrees of the Curie transition. This performance is not possible with other alloys, such as nickel copper, as its M vs. T curve decreases continuously with temperature.

The use of thermoseeds to heat tissue involves implanting an array of small (approximately 0.5 mm radius, 1 cm or more long) ferromagnetic seeds directly into the tissue. When the seeds are placed in an alternating magnetic field, heat is produced. The seeds may be left in the body following treatment so there is no need for further invasive procedures following implantation to extract them. Given the fact that the thermoseeds are to remain in the body, it is necessary to consider the potential toxicity of the ferromagnetic alloy employed. The toxicity of nickel has been well established. Severe allergic reactions among humans can result from contact with nickel and can cause hemolysis of human red blood cells through an apparent direct interaction between the red cell membrane and the Ni particle surface. The occurrence of copper toxicity, while somewhat infrequent, remains a problem. Acute copper poisoning can result in severe intravascular hemolysis resulting in jaundice and acute renal failure.

In that CoPd alloy has been in the past as an implantable substance, especially in dental prostheses, extensive toxicity evaluations have been made on the material revealing that such a binary alloy has only very weak cytotoxicity as compared to nickel and copper alloys.

It is accordingly a principal object of the present invention to provide a new thermoseed for use in treatment of tumors.

Another object of the invention is to provide a thermoseed formed from a ferromagnetic alloy that exhibits an increasing magnetization with temperature characteristic until its Curie point temperature is approached as the thermoseed is inductively heated upon exposure to an oscillating magnetic field.

Yet another object of the invention is to provide an inductively heated thermoseed comprised of an alloy that does not readily corrode in body fluids and is relative non-toxic.

Still another object of the invention is to provide a thermoseed formed from an alloy of cobalt and palladium where the percent of palladium in the alloy positions the Curie point within a therapeutic range without.-unduly broadening the Curie transition range.

SUMMARY OF THE INVENTION

The foregoing features, objects and advantages of the invention are achieved by providing a generally cylindrical ferromagnetic member having a predetermined radius and length dimension permitting implantation thereof in tissue to be treated where the ferromagnetic member exhibits a Curie point temperature in a therapeutic range of from about 41.5° C. up to 100° C. and further exhibiting an increasing magnetization vs. temperature characteristic until the Curie transitions zone is reached upon the heating up of the ferromagnetic member through the application of an oscillating magnetic field thereto. The therapeutic range can vary depending upon the nature of the tissue involved and the procedure being effected. In treatment of prostate tumors, the range may be from about 42° C. up to 65° C. whereas in ablating a portion of brain tissue causing seizures, the range may extend to 100° C. because of the vascularizaton in brain tissue.

A ferromagnetic material meeting the foregoing requirements is a binary alloy of cobalt and palladium whose atomic percent cobalt is in the range of from 8.5% to 11.0%.

The rate at which heat is produced by a cylindrical thermoseed depends upon the intensity and frequency of the applied magnetic field, the permeability of the alloy and on its radius. Generally speaking, the rate of heat production increases with an increase in any of the above parameters. It is also found that the heating power is a function of the orientation of the implant relative to the applied magnetic field. A perpendicular component of the applied field adds little to the heat production and, accordingly, in implanting the seeds into the tumorous tissue, an effort is made to orient the seed so that they will be parallel to the applied field. In arriving at the radius for the thermoseed, undue trauma to tissue during implantation is an important consideration.

DESCRIPTION OF THE PREFERRED EMBODIMENT

The literature describes the efficacy of using hyperthermia in the treatment of cancer. Therapeutic hyperthermia results when the temperature of living tissue rises above 41.5° C. resulting in negation of the body's natural temperature regulation. It is known that blood flow through tumors is typically at a lower rate than the flow through normal tissues. As a result, when heat is applied to a cancerous region, tumors tend to act as heat sinks. That is, they will absorb heat at a higher rate than surrounding, normal tissue and, thus, will experience a faster and higher rise in temperature. Hyperthermia is based on this principle and the fact that malignant cells cannot withstand heat as well as normal cells. The degree to which cellular replication can be interfered with depends not only on the treatment temperature, but also on the sensitivity of the cells. Replication of malignant cells is arrested by their intracellular reactions to heat. The resulting vascular damage within the tumor causes the region to become acidic and deprived of nutrients, which results in further difficulties in repairing damage.

A problem common to all hyperthermia systems is the occurrence of thermotolerance in which, after a first thermoshock, some of the surviving cells become more resistant to heat into the increased synthesis of certain proteins, sometimes referred to heat shock proteins. The degree of thermotolerance decreases with time following treatment, although it may take as long as 100 hours following treatment before the cells exhibit their preshock sensitivity. Also, a decreased rate of thermotolerance is observed when the cells are subjected to higher temperatures and/or a faster rise in temperature and/or longer times of exposure to heat.

The use of thermoseeds in exposing cancerous tissue to elevated temperatures lends itself to long-term, periodic treatments. In that the thermoseeds are permanently implanted into the cancerous tissue, the patient can be scheduled for activation of the thermoseeds at intervals of minimal thermotolerance. The use of thermoseeds to heat tissue involves implanting an array of small, typically 1 mm diameter ferromagnetic alloy members, each 1-2 cm in length, directly into the tissue to be treated. When the seeds are placed in an alternating magnetic field, the temperature of the seeds rises and the heat is conducted to the cancerous tissue.

In accordance with the present invention, the thermoseeds are formed from a CoPd alloy, especially formulated to provide a self-regulating temperature rise which falls into the therapeutic range in question when an external magnetic field is applied transdermally to the implanted seeds.

Figure 1:
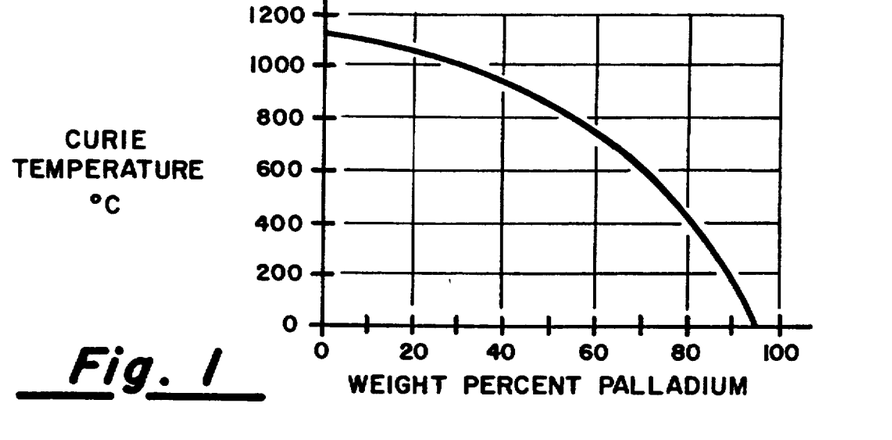
FIG. 1 is a plot showing the Curie point dependence of a CoPd alloy as a function of the weight percent cobalt in the alloy.
Figure 2:
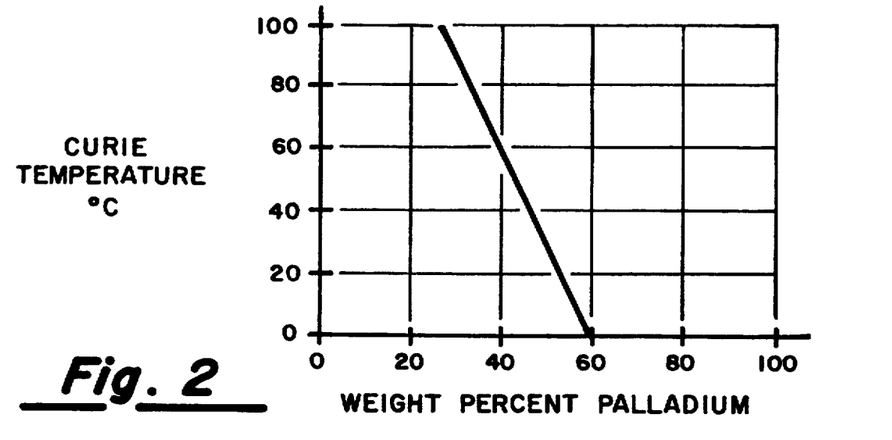
FIG. 2 is an enlargement of a portion of the curve of FIG. 1.

The composition of the CoPd ferromagnetic alloys for inducting hyperthermia use is determined by the Curie temperature transition of the alloy. FIG. 1 is a plot showing the Curie point dependence of the CoPd alloy as a function of the weight percent cobalt in the alloy. FIG. 2 is an enlargement of the region of interest of the curve of FIG. 1 as far as application to induction thermoseeds is concerned. From this plot, one can see that alloys with Curie temperatures ranging from 40° C. to 100° C. can be achieved by varying the composition of the CoPd alloy by adjusting the percent by weight of cobalt by only about 2%, i.e. from about 5% to 7% by weight of cobalt in the alloy. In that the plot of FIG. 2 is quite linear, it is possible to compute the sensitivity as about 1° C./0.033 wt. %. This is nearly three times more compositionally sensitive than nickel copper alloys which have been used in the past.

The CoPd alloy from which the thermoseeds are ultimately fabricated can be produced using conventional alloying procedures. Cobalt and palladium pellets or powders can be arc melted under inert gas (nitrogen or argon) in a carbon arc furnace. In this process, the alloy is arc melted on a water-cooled copper plate, and then remelted and cast into a cylindrical mold.

The compositional precision necessary for producing a specific Curie point may make arc melting for a precision Curie temperature difficult. Intense heat generation tends to cause metal powders to be ejected from the melt and, likewise, metal vaporization from the hot arc will alter the composition further. Palladium is found to have a rather high vapor pressure in liquid form, which can cause more Pd to be vaporized than Co during such melting, thus leading to compositions consistently higher in Co than anticipated.

We have found that an induction melting technique leads to a more uniform, predictable alloy. In this process, the metal pellets or powders of Co and Pd can be placed in a sealed crucible vessel under inert gas and melted using an induction coil. Being encapsulated, the powders cannot be sputtered and dispersed and, moreover, the vessel can be pressurized above the vapor pressure of Pd so that vaporization is also minimized. The crucible vessel in which the ingot is formed is designed so that the ingot will be cylindrical.

Figure 3:
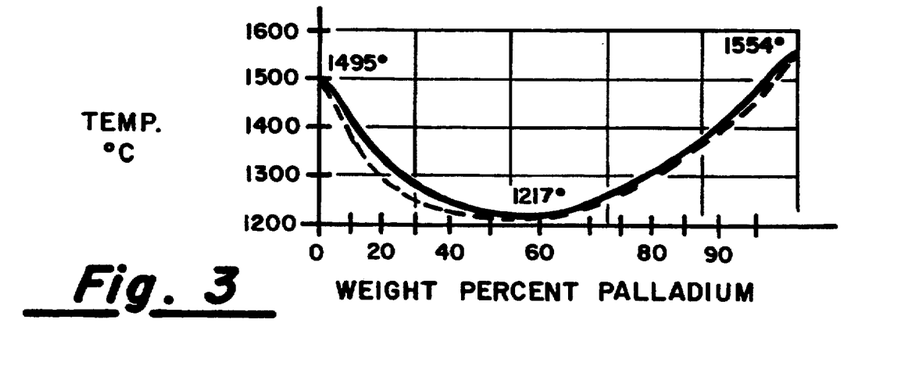
FIG. 3 is a binary phase diagram for a CoPd alloy.
Figure 4:
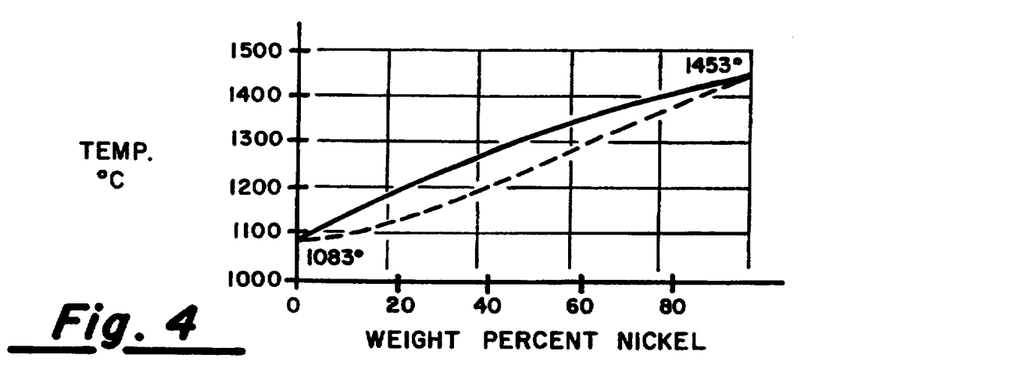
FIG. 4 is a binary phase diagram for a NiCu alloy.

The alloyed ingot cylinder, typically ¼ in. to ½ in. in diameter of the drawn wire, is then mechanically swaged and drawn into a desired predetermined diameter wire. With no limitation intended, the diameter may be in range of from 0.8 mm to 1.2 mm. Cold working of the alloy ingots into the wire, which are cut to length in creating the thermoseeds, creates a concern if any inhomogeneity is present within the original cylindrical ingot. Referring to FIG. 3, there is shown a binary phase diagram for a CoPd alloy. A small gap is seen to exist between the liquidus and the solidus lines (the LS gap) in the diagram around 1450° C. for a 94 wt. % Pd alloy. Above these lines, the alloy exists in a completely liquid state. Below the lines, it is a solid. In between the lines, both liquid and solid exist. Upon cooling through this region, a range of CoPd alloy compositions will be present. The first alloy to solidify is slightly palladium-rich, while the last alloy to solidify is cobalt-rich. As indicated earlier, only a 0.033 wt. % variance in the composition will change the Curie point by 1° C., and thus, the gap may be large enough to effect the magnetic transition properties. A similar diagram for NiCu is shown in FIG. 4 for comparison. Here, the LS gap is much larger, but the compositional sensitivity of this alloy is only 0.10 wt. % per degree C., which is about three times less sensitive than CoPd.

Variation in the composition of the material may be worsened as the wire is drawn out to smaller radii. Thus, it has been found beneficial to begin cold working the alloys after they have been fully homogenized. High temperature annealing of the alloy slightly below the melting point, at 1000°-1100° C. for a few hours, has proven to be sufficient for CoPd. If it is found that the metal hardens quickly with cold working, annealing may also be done during the wire drawing process.

After the wire has been fully drawn and cut into appropriate lengths, say 1-2 cm, the seeds are given one final heat treatment to allow recrystallization and grain growth following the cold working. This annealing step can be done in a single zone furnace under inert gas. The alloys are then furnace cooled to prevent oxidation upon exposure to an open-air environment. The cooling rate has been found to be irrelevant, so long as it is not so fast as to create local thermostresses in the metal that affects the metal properties thereof.

Figure 5A:
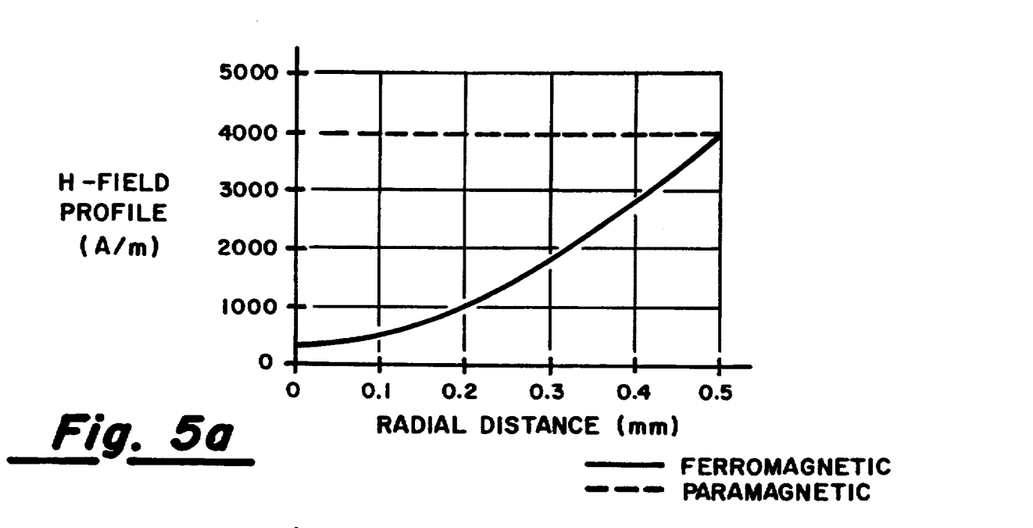
FIGS. 5(a) and 5(b) are plots showing variation in H-field profile and current density profile, respectively, as a function of the radius of a thermoseed cylinder from its periphery to its center.
Figure 5B:
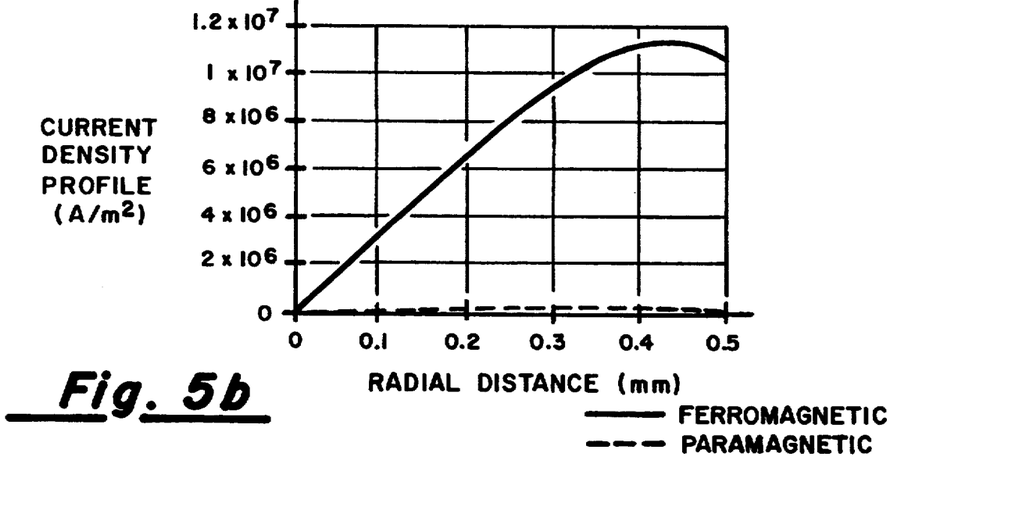

Having described a production method for the thermoseeds, the mechanism by which ferromagnetic alloy cylinders produce heat when exposed to an oscillating magnetic field will be presented to provide background on how the magnetic properties of the alloy affect heating. The analytical solution modeling the heating of ferromagnetic cylinders is rather complex, and is limited by the assumption that the magnetic permeability is invariant and independent of the applied field. The derivation relies upon a set of Bessel functions to provide the attenuation of the magnetic field within the cylinder. The attenuation of the applied H-field by the ferromagnetic cylinder produces eddy current heating. As illustrated in FIGS. 5(a) and 5(b), the induced eddy current density is directly dependent upon the gradient of the H-field with respect to the radius. The maximum which occurs in the current density curve of FIG. 5(b) seems contradictory to the nearly constant field attenuation over this range shown in FIG. 5(a). This maximum occurs because the circumference or cross-sectional area of the cylinder is also decreasing, and although the induced current in this range is nearly constant, the current density is increasing slightly. It is to be noted that although H-field is non-zero at R=0, the eddy current density must be 0 at the center of the cylinder.

The shape of the H-field attenuation profile, and thus the eddy current profile, determines the amount of power dissipated in the cylinder. For a long cylinder exposed to a sinusoidal magnetic field, the power output per unit length can be calculated by the equation:

$$P = \frac{\pi \cdot X \cdot H^2}{\sigma} \cdot \frac{ber(X) \cdot ber'(X) + bei(X) \cdot bei'(X)}{ber(X)^2 + bei(X)^2}$$

Where the variable x, the induction number as defined as:

$$X = r \cdot \sqrt{\omega \cdot \mu_o \cdot \mu_r \cdot \sigma}$$

as the ber and the bei functions are Bessel functions of Kelvin's form. If the assumption is made that $x \ll 1$, the power equation becomes:

$$P = \frac{\pi X^4 H^2}{16\sigma}$$

and for $x \gg 1$, the power equations becomes:

$$P = \frac{1}{\sqrt{2}} \cdot \frac{\pi X H^2}{\sigma}$$

Figure 6:
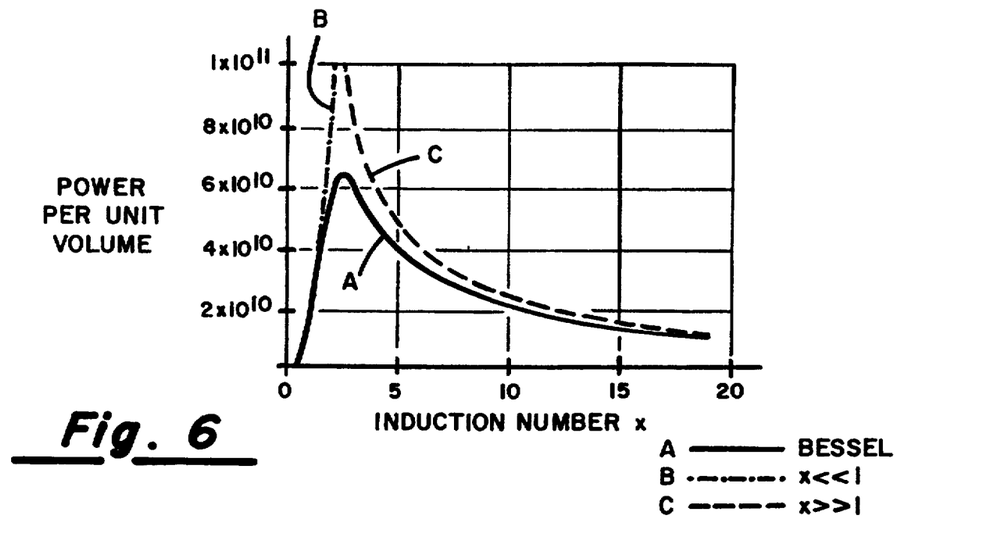
FIG. 6 is a plot of the power production per unit volume vs. induction number as a function of radius for cylindrical seeds inductively heated.

The comparison of these formulas vs. induction number, normalized to power per unit volume by dividing by $\pi \cdot R^2$ is illustrated in FIG. 6. A maximum occurs in the plot at $x=2.5$, indicating that an optimal power coupling per unit of volume of material is possible at this point. FIG. 6 represents the power production per unit volume vs. induction number (as a function of radius) for cylindrical seeds inductively heated. The curve labeled A indicates the true analytical solution while curve B is the approximation when x is assumed to be much, much less than 1 and curve C, the approximation when x is much, much greater than 1. For a specific material, the induction number is determined by the conductivity and permeability, leading the operating frequency and cylinder radius as the only variables that can be controlled.

The foregoing analysis does not consider one important factor, namely, the operating frequency which can be altered to reduce the value of x. An upper limit H-f product of $4.85 \times 10^8$ amp/mm-sec has been established for safe tolerance by human patients. This limit arises due to the induction of eddy current heating within the patient and the heat production at the skin surface for large patient diameters. The relationship dictates that any change in the frequency may be accompanied by an inverse change in the applied field strength. By maintaining this H-f product as a variable, the optimization analysis changes considerably.

Figure 7:
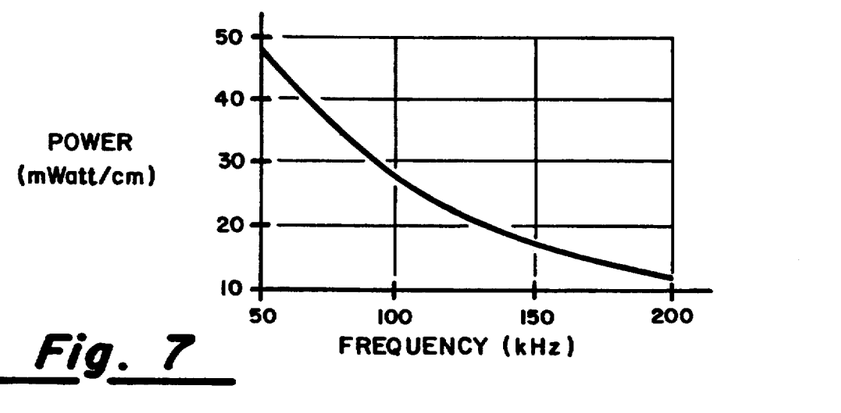
FIG. 7 is a plot showing power output versus field frequency at a constant H-f.

FIG. 7 is a plot showing power output vs. field frequency at a constant H-f for a 1 mm diameter cylinder with typical material constants. Maintaining the radius (and thus the volume) constant, and using typical values of conductivity and permeability for a thermoseed cylinder ($\rho = 2.4 \times 10^6 \, \Omega^{-1} \, m^{-1}$, $\mu_r = 15$), a plot of power output per unit length vs. frequency for a constant H-f product reveals no maximum in the power output. Power output increases with decreasing frequency and increasing H, as the power production is proportional to $H^2$.

The above analysis indicates that, given a limit or range of implant sizes to work with, the lowest frequency at constant H-f product will yield the highest output power for cylindrical thermoseeds. This analysis is limited by the linearity assumption that the $\mu$ is invariant with applied field strength.

Figure 8A:
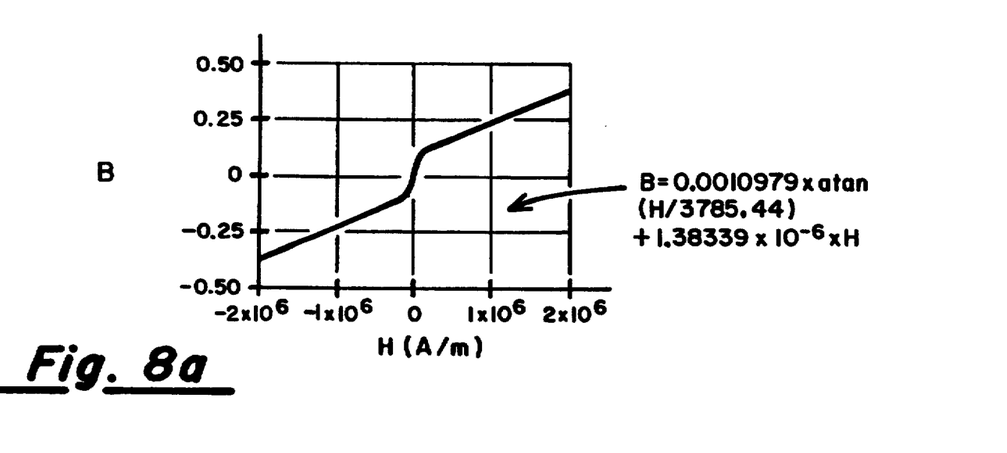
FIG. 8(a) is a B-H plot for CoPd hyperthermia alloy with a curve fit of the form $B = a(\arctan(H/b)) + cH$.
Figure 8B:
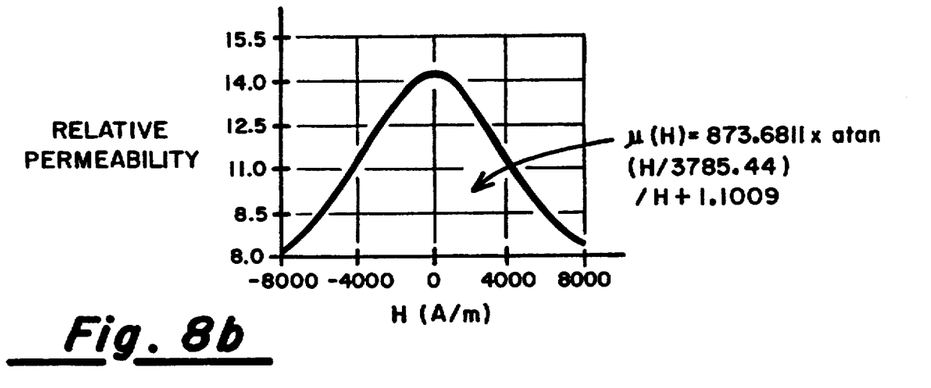
FIG. 8(b) is a plot of $\mu$ versus H derived from the curve of FIG. 8(a)

The previous derivations and analyses are all based upon an invariant model for the magnetic permeability. However, as previously indicated, this is generally not valid for a ferromagnetic material, and could lead to significant optimization error for weak magnetic alloys used as thermally regulating seeds. One method of correcting for a non-linearity is to determine the magnetic permeability at all field strengths within the applied field range. FIG. 8(a) is a B-H plot for a CoPd hyperthermia alloy at room temperature with a curve fit of the form $B = a(\arctan(H/b)) + ch$ where a, b and c are constants. The continuous function B(H) can then be used to approximate the relative permeability using the equation:

$$\mu_r(H) = B(H)/\mu_0 H$$

which is shown plotted in FIG. 8(b). It can be seen that the relative permeability drops off significantly at field strengths of 4,000–8,000 A/m, which corresponds to the maximum fields used at 100 and 50 kHz, respectively, for a H-f product of $4 \times 10^8$.

Figure 9:
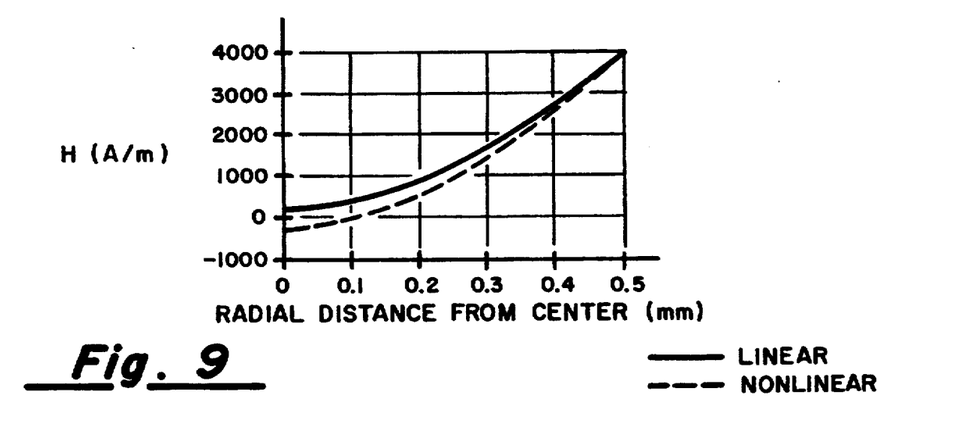
FIG. 9 is a plot of field strength versus radius of a CoPd cylindrical alloy seed when heated by a 100 Khz, 4000 A/m magnetic field comparing the linear and nonlinear H-field attenuation.

The non-linear eddy current heating analysis can be approximated through an iterative method, computing the H-field profile, assigning updated permeability values and repeating the process until the solution converges. The numerical H-field profile may be used to find the current density as a function of radius and integrated to estimate the total power output. A comparison of the H-field and relative permeability profiles in a CoPd cylinder in the non-linear approximation and the linear solution are illustrated in FIGS. 8 and 9. The non-linear analysis shows a clear change in the H-field attenuation through the cylinder, and thus predicts a change in current density and power output. FIG. 9 displays the field dependent permeability in the cylinder for the linear and non-linear solutions, the linear value corresponding to the applied field strength. This non-linear analysis predicts a 10% increase in implant power output over the linear case, according to the CoPd data of FIG. 7a, modeling a 1 mm diameter thermoseed.

Figure 10:
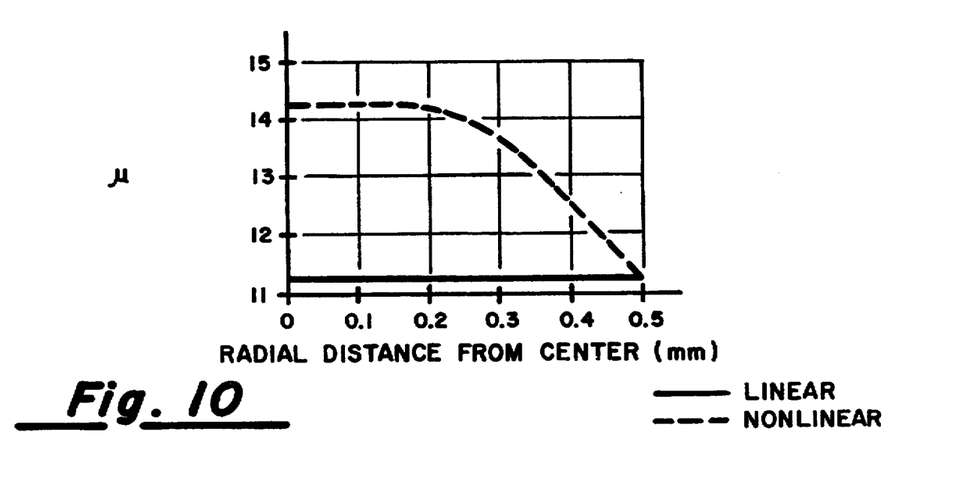
FIG. 10 is a plot of relative permeability versus radius comparison for linear and nonlinear modeling of the CoPd alloy in FIG. 9.
Figure 11:
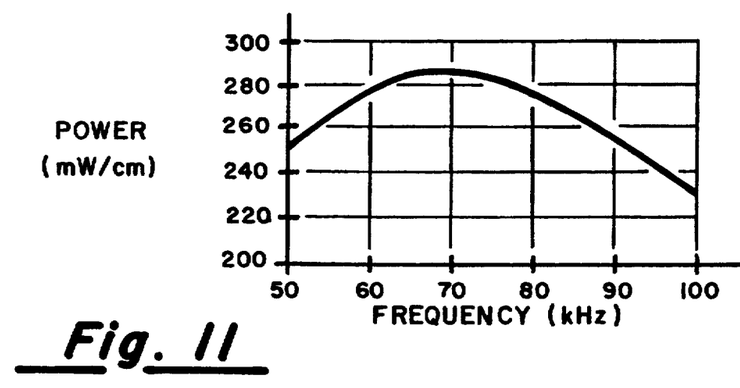
FIG. 11 is a plot of output power versus frequency for a CoPd alloy.

Using the iterative process from FIGS. 9 and 10 at various frequencies, the analysis for a constant Hf product of $4 \times 10^8$ amp/m-sec indicates that there is an optimal frequency for heating, as shown in the plot of FIG. 11. The output power is still dependent upon $H^2$, but the decrease in relative permeability at high fields (see FIG. 8(b)) offsets this effect. A more thorough analysis of the frequency optimization would use data points from B-H curves at many field strengths within the range of interest, rather than data from a single B-H wave.

Figure 12:
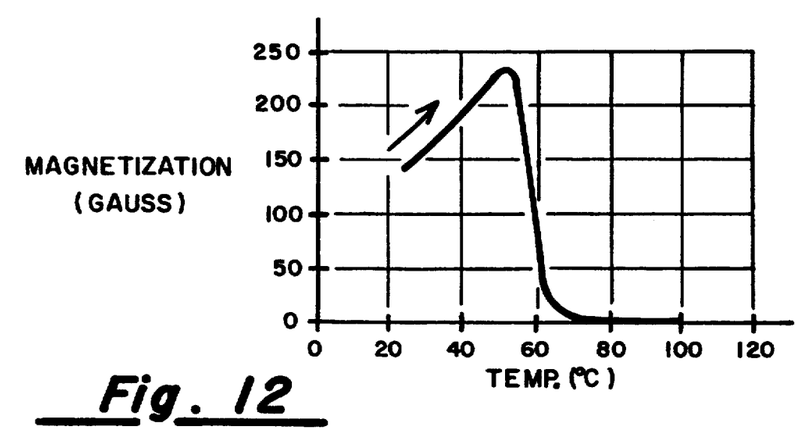
FIG. 12 is a magnetization versus temperature plot for CoPd showing a rising M vs. T characteristic below the Curie transition.
Figure 13:
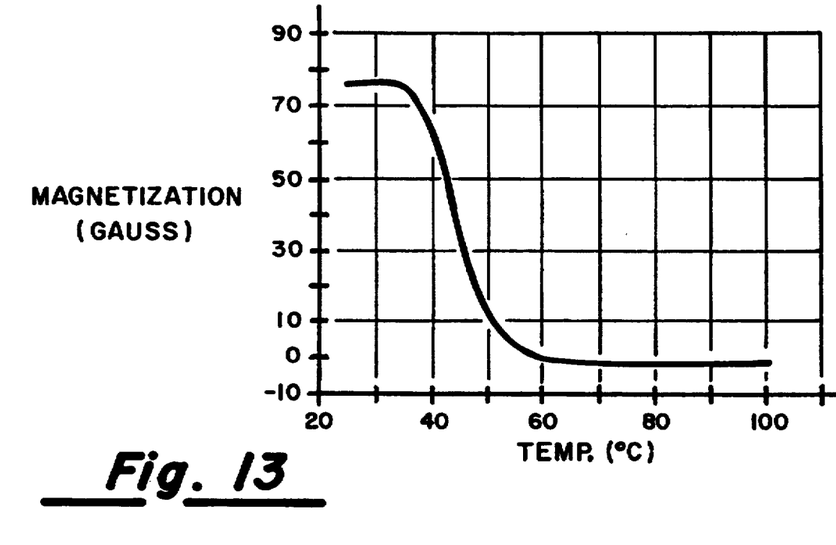
FIG. 13 is a magnetization versus temperature plot for a NiCu alloy.

It is important to note that the analysis of the CoPd alloy has not taken into consideration the temperature dependence of the magnetic properties. Optimization of the implants should provide the most efficient heating around the transition point. Experimental data plotting magnetization vs. temperature for the CoPd alloy indicates an interesting and rather unexpected result. With reference to FIG. 12 which shows a magnetization vs. temperature plot for CoPd at 55° C., it indicates a sharp rise in permeability as the Curie point is approached. In that the permeability of the alloy increases with temperature in a range slightly below the Curie point, the implant and heating system can be designed so that it will radiate more power as it heats up until the Curie transition point is reached. By optimizing the implant about this local peak in the M-T curve, a highly efficient on/off switch property results, with the maximum power output within a few degrees of the transition. This would require B-H curves of the alloy at the peak temperature for a range of applied field values. Such optimization is not possible with the NiCu alloy whose M vs. T curve is shown in FIG. 13 for comparison. Here, the curve decreases continuously with temperature. This property of having an increasing H vs. T. up until the Curie temperature is reached alone makes CoPd a superior candidate as an implantable thermoseed. Another advantage of CoPd is its corrosion resistance. In vitro studies of this alloy have been performed in mammalian Ringers solution to 7.0 corresponding to a simulated body environment, Because of the extremely low corrosion rate and minimal toxicity of CoPd ferromagnetic alloys, they are well tolerated in the body and this alloy is an excellent candidate for long-term implantation.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different formulations and devices, and that various modifications, both as to the composition details and operating procedures, can be accomplished without departing from the scope of the invention itself.

What is claimed is:

1. An implantable ferromagnetic thermoseed for treating tumorous tissue comprising:
   a generally cylindrical, ferromagnetic member having a predetermined radius and length dimension, said member exhibiting a Curie point temperature in a therapeutic range of temperatures and an increasing magnetization with temperature characteristic until said Curie point temperature is approached, said member adapted to produce inductive heat upon exposure to an oscillating magnetic field.

2. The implantable ferromagnetic thermoseed as in claim 1 wherein said ferromagnetic member is an alloy of cobalt and palladium.

3. The implantable ferromagnetic thermoseed as in claim 2 wherein said alloy is a binary alloy whose weight percent cobalt is in the range of from 4% to 7%.

4. An injectable ferromagnetic thermoseed for treating tumorous tissue comprising:
   a generally cylindrical ferromagnetic member having a predetermined length and radius, said member being an alloy of cobalt and palladium with the atomic percent cobalt being in a range yielding a Curie point temperature in the range of from about 42° C. to about 100° C., said member adapted to produce inductive heat upon exposure to an oscillating magnetic field.

5. The injectable ferromagnetic thermoseed as in claim 4 wherein said predetermined radius lies in the range of from 0.2 mm to 2.0 mm and said predetermined length is in a range of from 5 mm to 50 mm.

6. The injectable ferromagnetic thermoseed as in claim 4 in which said alloy exhibits an increasing magnetization with temperature characteristic until said Curie point temperature is approached.

7. A method of thermally treating cancerous tissue in a body of a patient, comprising the steps of:
   (a) providing a plurality of cylindrical ferromagnetic members of a predetermined radius and length dimension, said members being an alloy of cobalt and palladium whose percent by weight of cobalt yields a Curie point temperature in a therapeutic range;
   (b) implanting said members at regularly spaced locations within said cancerous tissue; and
   (c) subjecting said members to an oscillating magnetic field aligned generally parallel to said length dimension of said members from a location outside of the body of the patient, the frequency of said oscillating magnetic field and the field strength thereof producing continuously increasing heat energy output from said implanted members to surrounding tissue by conduction from said implanted members, until the Curie point of the alloy is reached.

8. The method as in claim 7 wherein the frequency of said oscillating magnetic field is in the range of from 50 kHz to 200 kHz.

9. The method as claim 7 wherein said Curie point temperature is in the range of from 40° C. to 100° C.

10. The method as in claim 7 wherein the alloy is a binary alloy whose weight percent cobalt is in the range of from about 4% to about 7%.

* * * * *